United States Patent
Tjahjadi et al.

(10) Patent No.: US 6,405,579 B1
(45) Date of Patent: Jun. 18, 2002

(54) SCALELESS ON-LINE RHEOMETER DEVICE

(75) Inventors: Mahari Tjahjadi, Evansville, IN (US); Joseph M. H. Janssen, Bergen op Zoom (NL); George F. Fischer, Vernon, IN (US); Ye-Gang Lin, Evansville, IN (US); Safwat E. Tadros, Evansville, IN (US); Galina D. Georgieva, Evansville, IN (US); Scott S. Haraburda, Vernon, IN (US)

(73) Assignee: General Electric Company, Pittsfield MA ( * ) Notice: Subject to any disclaimer, the term of this patent is extended or adjusted under 35 U.S.C. 154(b) by 0 days.

(21) Appl. No.: 09/394,481

(22) Filed: Sep. 11, 1999

Related U.S. Application Data

(63) Continuation-in-part of application No. 08/920,944, filed on Aug. 29, 1997, now Pat. No. 5,974,866.

(51) Int. Cl.⁷ .......................... G01N 11/04; A23G 1/22
(52) U.S. Cl. ........................ 73/54.11; 425/115
(58) Field of Search .......................... 73/54.01, 54.04, 73/54.11, 54.13, 54.14; 425/115; 264/40.1

(56) References Cited

U.S. PATENT DOCUMENTS

| | | |
|---|---|---|
| 3,048,030 A | 8/1962 | De Haven |
| 3,203,225 A | 8/1965 | Sieglaff et al. |
| 3,252,320 A | 5/1966 | Welty |
| 3,832,886 A | 9/1974 | Pliskin |
| 4,213,747 A | 7/1980 | Friedrich |
| 4,241,602 A | 12/1980 | Han et al. |
| 4,403,502 A | 9/1983 | Lindt |
| 4,449,395 A | 5/1984 | Kurtz et al. |
| 4,626,186 A | 12/1986 | Hofstetter et al. |
| 4,733,970 A | 3/1988 | Yokana |
| 4,817,416 A | 4/1989 | Blanch et al. |
| 4,933,886 A | 6/1990 | George |
| 4,954,302 A | 9/1990 | Marchildon et al. |
| 4,992,487 A | 2/1991 | Rao |
| 5,347,851 A | 9/1994 | Mode |
| 5,347,852 A | 9/1994 | Grudzien et al. |
| 5,456,105 A | 10/1995 | James |

*Primary Examiner*—Daniel S. Larkin
*Assistant Examiner*—J L Politzer

(57) ABSTRACT

A system for providing process control information, such as viscosity, concerning a polymer melt comprises a means containing a polymer melt under pressure; means for diverting a stream of the polymer melt directly from said containing means to and through an orifice of predetermined geometrical shape wherein the flow of said diverted portion to and through said orifice is unobstructed and directly dependent on the pressure of said main polymer melt wherein the cross sectional area is sized to permit the flow of said diverted melt polymer therethrough absence additional independent means acting on said diverted melt polymer for increasing flow through said orifice; temperature sensing means for measuring the temperature of the diverted melt stream and producing a resultant temperature signal; pressure sensing means for measuring the pressure of the diverted melt stream and producing a resultant pressure signal, said pressure signal being directly dependent on the pressure of polymer in said main polymer melt and the predetermined size of said orifice; means measuring or calculating the production rate of the extruder; and manufacturing control system means responsive to the temperature, pressure and production rate signals for determining process characteristics of the main polymer melt.

14 Claims, 2 Drawing Sheets

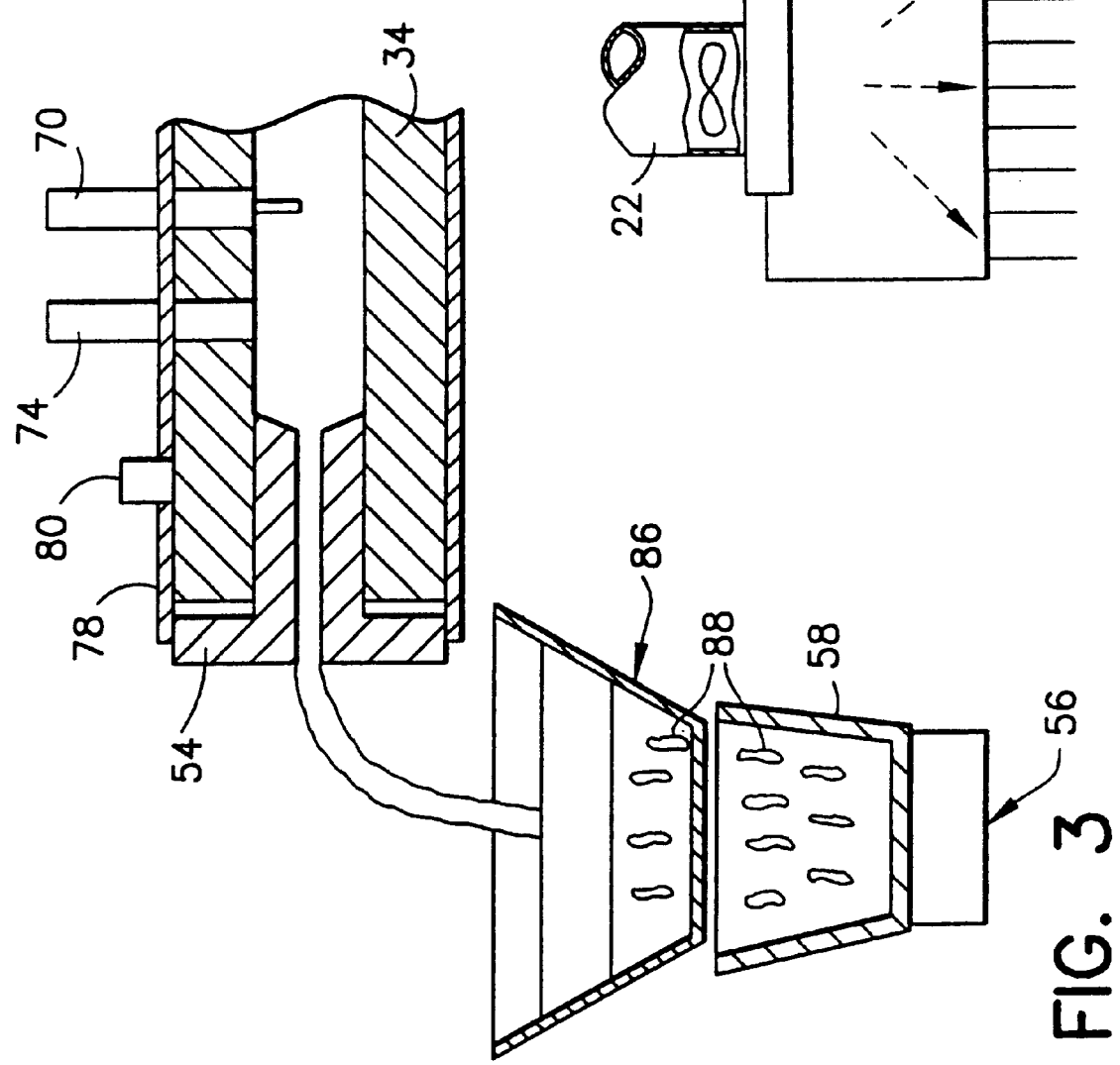

SCALELESS ON-LINE RHEOMETER DEVICE

CROSS REFERENCE TO RELATED APPLICATIONS

This application is a continuation-in-part of U.S. Ser. No. 08/920,944 filed Aug. 29, 1997 now U.S. Pat. No. 5,974,866 entitled, ON-LINE RHEOMETER DEVICE.

BACKGROUND OF THE INVENTION

1. Field of the Invention

The present invention relates generally to the measurement of process characteristics of melted materials and pertains, more specifically, to the on-line measurement of such characteristics as the viscosity of polymer melts for purposes of monitoring and controlling of manufacturing processes involving molten plastics.

2. Description of the Prior Art

Rheological testing equipment has been available for a very long time in conducting laboratory measurements of certain important characteristics of polymer melts used in various manufacturing processes. Thus, such properties as viscosity and melt flow index are being measured in the laboratory with increasing accuracy. More recently, efforts have been directed toward the measurement of these characteristics on-line, during the manufacturing process itself, in order to provide constant, closer control over the quality of the melt utilized in the process. On-line measurement requires equipment which not only is relatively easy to use and maintain, but which is rugged enough to withstand the operating conditions to which the equipment will be exposed. In order to be effective, the equipment must be responsive, and must avoid disturbing the manufacturing process being monitored.

Among the more successful on-line rheometers available currently are capillary rheometers which divert a portion of the polymer melt from the main stream of molten plastic, conduct measurements on the diverted melt, and then simply purge the melt out to the atmosphere, hence called A on-line rheometer. Also, rheometers have been developed in which the diverted melt is returned to the main stream, hence called A at(or in)-line) rheometer, thereby eliminating additional steps associated with the purge stream. Both on-line and in-line rheometers usually employ a first metering pump, such as a gear pump, to feed a capillary passage with a controlled flow of the diverted melt, and in case of in-line, a second metering pump to return the diverted melt to the main stream. Pressure drop along the capillary passage is measured and the temperature of the diverted melt is closely controlled with an independent heating or cooling arrangement in order to measure viscosity, as a function of the measure of the pressure drop, to gain the information necessary to control the process.

For a more complete understanding of the state of the technology with respect to rheological testing, consider some instances of known methods and apparatus as reflected by the patent literature. U.S. Pat. No. 4,817,416 to Blanch et al. discloses a system for making in-line rheological measurements utilizing a rheometer of the type in which a first metering pump delivers diverted melt from a process main stream to a capillary passage and a second metering pump returns the diverted melt from the capillary passage to the process main stream and the viscosity of the diverted melt is measured by controlling the rate of flow of the melt to maintain constant the pressure drop between spaced apart locations along the capillary passage and measuring the temperature of the melt in the capillary passage. The measurements may be made while controlling the speed of the second metering pump independent of the speed of the first metering pump to maintain the pressure at the exit of the capillary passage essentially constant. The capillary passage is placed in close proximity to the process main stream for maintaining a relatively short residence time during which the diverted melt resides outside the process main stream so as to attain a relatively quick response to changes in the measured viscosity.

U.S. Pat. No. 4,449,395 to Kurtz et al. discloses a system for testing thermoplastic material according to which a fractional, continuous, molten and flowable sample of the material is passed as a stream to and successively through each of either a controllable pumping zone maintained at constant temperature and pressure or controllable pressure zone maintained at constant flow rate and temperature, and a die zone to form a continuous strand of the material. The viscosity of the material in the pumping and die zones is measured. A measurement of elasticity is provided by obtaining a measurement of percentage of cross-section area swell in the strand in passage from the die zone over a constant length distance downstream of a point of mark sensing. The viscosity measurement is combined with the elasticity measurement to provide fuller Theological characterization data for the material.

U.S. Pat. No. 4,403,502 to Lindt discloses a motionless viscometer and associated method for resinous materials including polymeric foams and non-resinous materials includes a reservoir section, a receiver section and an interposed tube. As the foam is expanded, the axial pressure within the connecting tube is measured as is the rate of rise of the foam within the receiver element. Shear viscosity and density as functions of time may be determined.

It was with knowledge of the foregoing that the present invention has been conceived and is now reduced to practice.

SUMMARY OF THE INVENTION

A system for providing process control information concerning a polymer melt comprises: means containing a polymer melt under pressure; means for diverting a stream of said polymer melt directly from said containing means to and through an orifice of predetermined cross sectional area wherein the flow of said diverted portion to and through said orifice is unobstructed and directly dependent on the pressure of said main polymer melt, said cross sectional area being sized to permit the flow of said diverted melt polymer therethrough absence additional independent means acting on said diverted melt polymer for increasing flow through said orifice; temperature sensing means for measuring the temperature of the diverted melt stream and producing a resultant temperature signal; pressure sensing means for measuring the pressure of the diverted melt stream and producing a resultant pressure signal, said pressure signal being directly dependent on the pressure of polymer in said main polymer melt and the predetermined size of said orifice; means of measuring the production rate of the extruder; and manufacturing control system, such as a Programmable Logic Controller (PLC), means responsive to the temperature, pressure and production rate signals for determining process characteristics of the main polymer melt.

In the present invention, the flow of the diverted steam is unobstructed and characterized by the absence of pumps or other pressure enhancing devices which might be employed to increase the pressure in the diverted stream. The orifice is sized to provide for substantially continuous flow of polymer melt therethrough with the pressure differential provided by the pressure in the main polymer melt and the pressure at the orifice outlet which is typically atmospheric pressure. Preferably the orifice opening has a diameter of about 0.05 to about 0.15 inch or if the opening is non-circular an equivalent cross-seasonal area. The means containing the polymer melt is preferably an extruder. A single Screw or twin screw extruder having a Length to Diameter ratio from bout 5 to about 60, and preferably from about 20 to about 40, a pressure in the extruder of polymer melt is greater than about 20 pounds per square inch and is typically within the range of about 600 to about 2000 pounds per square inch, more typically within the 800 to 1400 range, and an extruder diameter of about ¾ to 16, preferably about 1 to about 8 inches are preferred features.

With the above system a passage extends between an inlet communicating with the main polymer melt and the outlet at the orifice. In the most preferred embodiment, the passage comprises a barrel member extending between inlet and outlet ends selectively attached at said inlet to said main polymer melt. The orifice comprises an insert mounted internal to the outlet end of the barrel. A heater means may be provided for maintaining substantially constant temperature of the passageway. In the situation where the orifice is located at a location remote from the extrude&, preferably it is located within about 5 inches of the extruder, the pressure measurement means and the temperature measurement means are adjacent or at least in very close proximity to the orifice to measure tie pressure drop across the orifice and the melt temperature at that location.

In the most preferred embodiment, the present invention relates to a system for providing process control information, such as viscosity, concerning a polymer melt comprises a barrel member extending between inlet and outlet ends which is selectively attached to a conduit containing a main stream of the polymer melt. The barrel member is adapted to receive at its inlet end a diverted melt stream from the conduit and is provided with temperature and pressure sensors for measuring the temperature and pressure, respectively, of the diverted melt stream. A capillary orifice is provided at the outlet end of the barrel member for receiving, then discharging, the diverted melt stream. As discharged, the melt stream may be at least partially solidified. A system in place to measure or calculate the total production rate through the extruder. A manufacturing control system is responsive to signals received from the temperature, pressure and production rate sensors for determining the process characteristics of the main stream of the polymer melt. A heater jacket preferably surrounds the barrel member for maintaining its temperature substantially constant. The capillary orifice has an L/D which is greater than about 3:1. The diverted melt stream transforms into at least partially solidified material after it is discharged from the capillary orifice and may be dropped onto a receptacle surface which is continuously weighed.

The invention is directed to an on-Line rheometer device capable of measuring melt viscosities of glass and/or mineral filled and unfilled thermoplastic resins. Preliminary results of several different glass filled flame retardant and non flame retardant grades from a manufacturing pilot line have indicated that differences between the on-line and quality assurance laboratory measurements are within the standard deviation of the laboratory measurement itself.

In order to improve critical to quality variables such as viscosity, flow consistency, and laboratory response time, prior to the present invention, it was realized that an in-/on-line rheometer would be highly desirable. When addressing the problem which led to the invention, the expectations were: (a) the improved rheometer has to produce transformable data "apples to apples", from in/on-line to the quality assurance laboratory; and (b) the device has to be robust, user friendly, and simple for quick mounting, and easy maintenance.

Previously, commercially available in/on line rheometer can not meet the expectations recited in (a) and (b) above. The difficulties lay with the inability of the components in known rheometers, such as gear pumps, stress transducers, sensors and other moving parts to withstand the wear caused by abrasive fillers such as glass fibers and minerals. The goal, then, realized by the invention, was to provide a device capable of measuring the melt viscosity of unfilled, and glass and or mineral filled resins in real time that would provide "apples to apples" comparison with quality assurance laboratory data. The resulting device is robust, easy to maintain, user friendly, and can be coupled and decoupled quickly from the die head. The melt flow through the rheometer is naturally self-cleaning and hence it does not require physical clean up between grades of polymer melt material. It is also desirable to reduce wear.

The on-line rheometer device of the invention comprises a modified die head, a capillary orifice, pressure and temperature sensors located upstream of the orifice, an option of a mini-pelletizer or grinder, a stationary or rotating receptacle, and a weight recorder. The heart of the rheometer is the capillary orifice with L/D>~3:1 where L and D are length and transverse dimension, perhaps diameter, respectively.

The conduit containing a main stream of the polymer melt, or possibly he die head may be modified by drilling a small hole, perhaps 0.5 inch in diameter, into the conduit to tap into the main stream thereby forming a side stream, then adding a barrel extension to the side stream with a capillary orifice threaded in or mounted at its exit. The rheometer barrel that is extended out of the die head is wrapped with a heater jacket to prevent heat loss or gain. A very small fraction of the polymer melt is diverted to the rheometer barrel and the capillary. The air-cooled plastic is then discharged. The response of the rheometer is minutes after making setpoint adjustment. To lengthen the interval required to empty the receptacle, the receptacle may be rotated, or a grinder/pelletizer may be used, or both.

Pressure and temperature transducers and a production rate output, such as feeder rates, send respective output signals (pressure, P, temperature, T; and production rate, MR, respectively) to the manufacturing control system. The manufacturing control system carries out pre-programmed tasks to convert the signals to viscosities. These tasks include execution of certain mathematical functions or algorithms derived from fundamentals of fluid mechanics and rheology.

The rheometer just described, unlike commercially available options, does not require that the pressure and temperature in the die head and in the capillary be controlled. The algorithm to calculate real tic viscosity, from P, T, and MR, is unique and the constants used in the algorithm are characteristics of the product and thus referred to as signatures. The rheometer's capillary orifice enables "apples to apples" comparison with quality assurance data since the melt viscosity rheometers used in the quality assurance laboratory are based on capillary geometry (for example, a melt flow indexer described in ASTM D1238). The elimination of the gear pump also greatly increases the flexibility and durability of the rheometer of the invention.

The present invention has several features and provides a number of advantages, some of which are summarized as follows: it enables truly on-line measurements for attaining quicker response and more accurate control of manufacturing processes involving polymer melts; mounts easily to a large variety of polymer processors such as single and twin screw extruders as well as any other continuous mixers and kneaders; permits the conduct of on-line measurements with a minimal intrusion and no contamination of the main process stream being monitored; permits increased versatility in the nature and extent of the information derived from on-line measurements of polymer melts, as well as increased accuracy in the information itself; enables ease of installation and use in connection with current manufacturing equipment and techniques; allows ready adaptation for use in connection with a wide variety of materials and operating conditions; provides a convenient station for additional sensing and observation devices available for monitoring the quality of the polymer melt and integration with manufacturing processes via feedback loop controller facilitates cleaning and general maintenance, as well as replacement of component parts either for repair or adaptation to specific materials and operating conditions; and provides a simple and rugged construction without moving parts for economical manufacture and reliable long term service. This data may be used as an input for the determination of the viscosity on a continuous basis. An advantage of this technique is a reduction in weight variability which might occur when using the stationary receptacle.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 2 is a diagrammatic illustration of a die head usable with the system illustrated in FIG. 1; and FIG. 3 is a detail view of some parts illustrated in FIG. 1 but illustrating another embodiment thereof.

DESCRIPTION OF THE INVENTION

Figure 1:
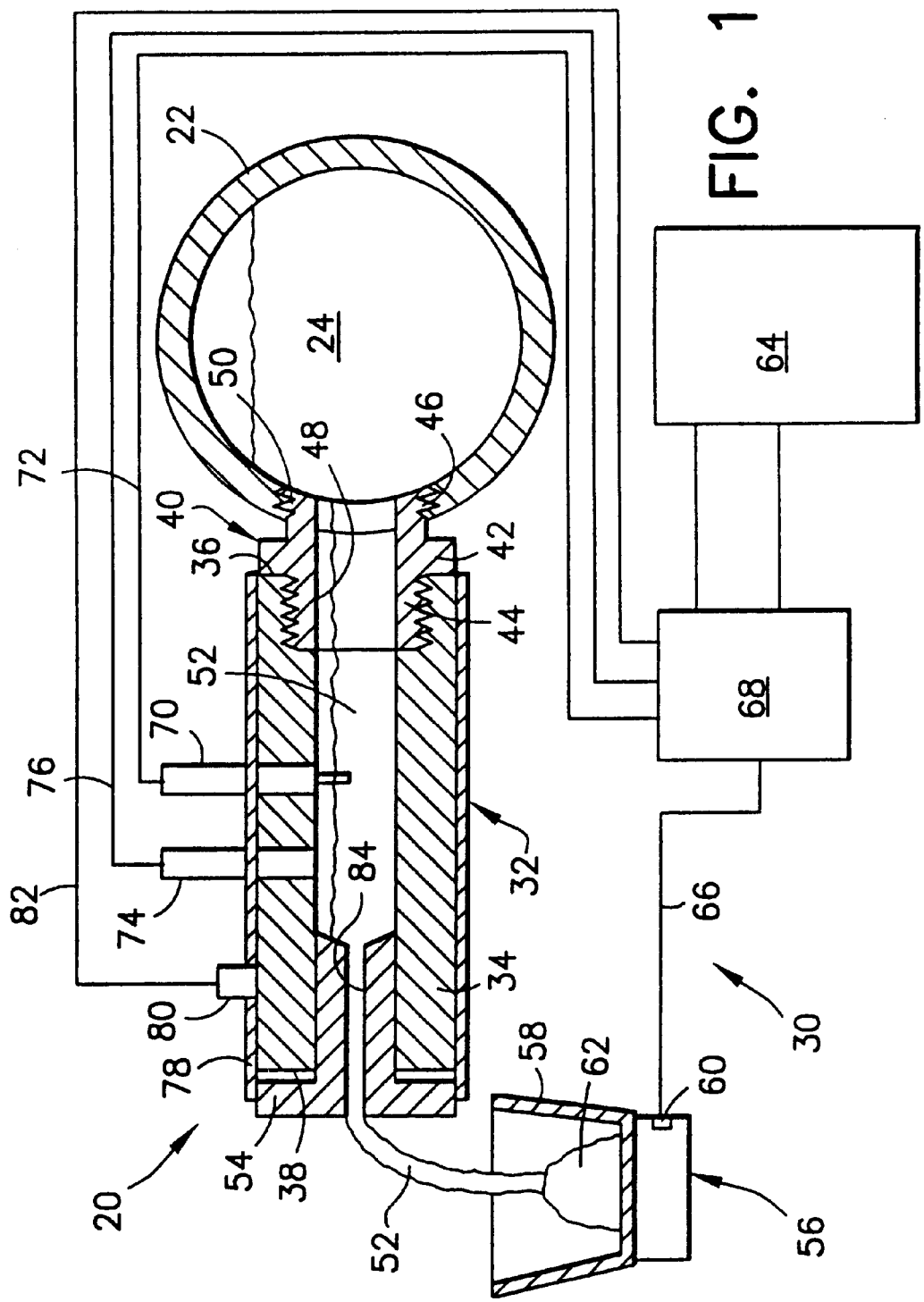
FIG. 1 is a schematic diagram, certain parts being cut away and shown in section, illustrating a system, embodying the present invention, for providing process control information concerning a polymer melt.

Turn now to the drawings and, initially, to FIG. 1 which diagrammatically illustrates part of a plastics extrusion machine 20 including a conduit 22 containing a main stream 24 of polymer melt terminating at a die head 26 (FIG. 2) of a polymer extruder which produces a plurality of polymer strands 28. The plastics extrusion machine 22 includes a system 30 for providing process control information concerning the polymer melt.

In turn, the system 30 includes an on-line rheometer device 32 which, in one instance, may be operably attached to the conduit 22 (FIG. 1) or, in another instance, may be operably attached to the die head 26 itself (FIG. 2). In either instance, a barrel member 34 extends between an inlet end 36 and an outlet end 38. The barrel member is selectively attached to the conduit 22 (or to the die head 26) by means of a suitable fitting 40 such as one, for example, which has a central peripheral flange 42 separating an outer threaded nipple 44 from an inner threaded nipple 46. The fitting 40 has a longitudinally extending bore 48 therethrough which is coaxial and transversely coextensive with a longitudinal bore 50 extending the length of the barrel member 34 when the nipple 44 is threadingly engaged with the inlet end of the barrel member.

A tapped hole 50 is suitably formed in the sidewall of the conduit 22 (or in the die head 26) for the threaded reception by the nipple 46. In this manner, the barrel member 34 is adapted to receive at its inlet end 36 a diverted melt stream 52 from the conduit 24. A capillary orifice or nozzle 54 is suitably fitted or mounted onto the outlet end 38 of the barrel member for receiving, then discharging, the diverted melt stream 52. Similarly, a temperature sensor 70 for measuring the temperature of the diverted melt stream 52 is mounted on the barrel member 34 and produces a resultant temperature signal advanced to the computer 64 via a lead 72 and the in/out device 68. Again, a pressure sensor 74 for measuring the pressure of the diverted melt stream 52 is also mounted on the barrel member 34 and produces a resultant pressure signal advanced to the manufacturing control system. The manufacturing control system is responsive to the temperature, pressure and production rate signals for determining process characteristics of the main stream of the polymer melt.

For purposes of the invention, a preferred process characteristic to be determined is the melt viscosity of the main stream 24 of the polymer melt. This may be represented by the following relationship:

$$OOL = B*)p*R4/8L*Q$$

where
OOL=on-line melt viscosity
B=a constant, 3.14159
)p/L=pressure drop across capillary orifice 54
R=orifice radius
Q=flow rate (volume/time)=function of MR.

Another representative formula for calculating the relationship between the various variables is as follows:

$$\eta_{OL} = \pi \rho R^4 p / 8LW$$

$\eta_{OL}$=on-line melt viscosity
$\pi$=a constant, 3.14159
$\rho$=pressure drop across capillary orifice 54
R=orifice radius
L=the length of the orifice
$\rho$=polymer melt density
W=polymer mass flow rate=function of MR It is desirable for the barrel member 34 to be provided with a suitable heater jacket 78 for maintaining substantially constant the temperature of the barrel member. In this regard, a second temperature sensor 80 for measuring the temperature of the barrel member 34 is also mounted on the barrel member and produces a resultant second temperature signal advanced to the manufacturing control system. The manufacturing control system is responsive to the temperature measurement provided by the sensor 80 for controlling energization of the heater jacket 78 to properly maintain the temperature of the barrel member and thereby minimize the temperature gradient of the diverted melt stream 52.

The capillary orifice 54 has a discharge channel 84 defined by a length L and a transverse dimension D which would be the diameter for a circular cross section. Preferably, for purposes of the invention, the ratio of L to D is greater than about 3:1, while the smallest ratio used in the laboratory rheometer is about 3, a larger ratio is preferred to minimize entrance and exit effects.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A system for providing process control information concerning a polymer melt comprising:

means containing a polymer melt under pressure;

means for diverting a stream of said polymer melt directly from said containing means to and through an orifice of predetermined cross sectional area wherein the flow of said diverted portion to and through said orifice is unobstructed and directly dependent on the pressure of said main polymer melt, said cross sectional area being sized to permit the flaw of said diverted melt polymer therethrough absence additional independent means acting on said diverted melt polymer for increasing flow through said orifice;

temperature sensing means for measuring the temperature of the diverted melt stream and producing a resultant temperature signal;

pressure sensing means for measuring the pressure of the diverted melt stream and producing a resultant pressure signal said pressure signal being directly dependent on the pressure of polymer in said main polymer melt and the predetermined size of said orifice;

mean for obtaining a production rate of an extruder, from sensor readings from feeder rates of the polymer melt entering the extruder; and manufacturing control system means responsive to the temperature, pressure and production rate signals for determining process characteristics of the main polymer melt.

2. A system as set forth in claim 1 wherein the means for obtaining the production rate calculates the production rate from the following mathematical equation:

$$\eta_{OL} = \pi \rho R^4 p / 8LW$$

where, $\eta_{OL}$=on-line melt viscosity, $\pi$=a constant, 3.14159, p=pressure drop across, capillary orifice 54, R=orifice radius, L=the length of the orifice, $\rho$=polymer melt density, and W=polymer mass flow rate=function of MR.

3. A system as set forth in claim 1 wherein said orifice sized to provide for substantially continuous flow of polymer melt therethrough.

4. A system as set for in claim 1 wherein said orifice is sized to correspond to an opening having a diameter of about 0.05 to about 0.15 inch.

5. A system as set forth in claim 3 wherein said means containing a polymer melt comprises an extruder.

6. A system as set forth in claim 5 wherein said extruder comprises a single or twin screw extruder.

7. A system as set forth in claim 5 wherein said extruder has a Length to Diameter ratio from about 5 to about 60.

8. A system as set forth in claim 5 wherein the pressure of polymer melt in said extruder is greater than about 20 pounds per square inch.

9. A system as set forth in claim 5 wherein said extruder has a diameter of about ¾ to about 16 inches.

10. A system as set forth in claim 3 wherein a passage extends between an inlet communicating with said main polymer melt and said an outlet at said orifice.

11. A system as set forth in claim 10 wherein said passage comprises a barrel member extending between inlet and outlet ends selectively attached at said inlet to said main polymer melt, said orifice comprising an insert mounted internal the outlet end of said barrel.

12. A system as set forth in claim 10 including:

heater means for maintaining substantially constant the temperature of said passageway.

13. A system as set forth in claim 10 wherein said orifice has a discharge channel defined by a length L and a transverse dimension D; and wherein the ratio of L to D is greater than about 3:1.

14. A system as set forth in claim 1 wherein said manufacturing computer system means is responsive to the temperature, pressure and production rate signals for determining the melt viscosity of the main stream of the polymer melt.

* * * * *